United States Patent
Gupta et al.

(10) Patent No.: US 11,786,894 B2
(45) Date of Patent: Oct. 17, 2023

(54) WHOLE BLOOD SEPARATOR DEVICE AND METHOD OF USE

(71) Applicants: Ashim Gupta, Lawrenceville, GA (US); Charles Bradley Simons, Milton, GA (US)

(72) Inventors: Ashim Gupta, Lawrenceville, GA (US); Charles Bradley Simons, Milton, GA (US)

( * ) Notice: Subject to any disclaimer, the term of this patent is extended or adjusted under 35 U.S.C. 154(b) by 435 days.

(21) Appl. No.: 17/083,384

(22) Filed: Oct. 29, 2020

(65) Prior Publication Data

US 2022/0134328 A1     May 5, 2022

(51) Int. Cl.
*B01L 3/00*     (2006.01)
*B04B 5/04*     (2006.01)

(52) U.S. Cl.
CPC .......... *B01L 3/5021* (2013.01); *B04B 5/0414* (2013.01); *B01L 2200/025* (2013.01); *B01L 2200/0652* (2013.01); *B01L 2200/0689* (2013.01)

(58) Field of Classification Search
CPC ............. B01L 3/5021; B01L 2200/025; B01L 2200/0652; B01L 2200/0689; B01L 3/50215; B04B 5/0414; A61M 1/029; A61M 2202/0427; A61M 1/3693; B01D 2221/10; B01D 21/262; G01N 33/491
See application file for complete search history.

(56) References Cited

U.S. PATENT DOCUMENTS

| | | | |
|---|---|---|---|
| 3,355,098 A | 11/1967 | Farr | |
| 3,513,976 A | 5/1970 | James | |
| 3,620,677 A | 11/1971 | Ayers | |
| 3,653,837 A | 4/1972 | Luks et al. | |
| 3,807,955 A | 4/1974 | Note | |
| 3,850,174 A | 11/1974 | Ayres | |
| 3,902,964 A | 9/1975 | Greenspan | |
| 4,227,620 A | 10/1980 | Conway | |
| 4,386,613 A * | 6/1983 | Locsei | A61D 3/00 604/327 |
| 4,411,163 A | 10/1983 | White | |
| 4,765,962 A | 8/1988 | Heim | |
| 4,861,477 A * | 8/1989 | Kimura | B01L 3/5021 422/918 |
| 6,506,167 B1 | 1/2003 | Ishimito et al. | |

(Continued)

FOREIGN PATENT DOCUMENTS

CN     207941543     10/2018
CN     210522545     5/2020

*Primary Examiner* — Walter D. Griffin
*Assistant Examiner* — Shuyi S. Liu
(74) *Attorney, Agent, or Firm* — David L. King (57) ABSTRACT

A whole blood separator device has a sleeve. The sleeve has a sleeve body. The sleeve body has an enlarged first proximal end portion and an enlarged second distal end portion and an intermediate cylindrical tube portion connecting the first proximal end portion and the second distal end portion. The sleeve body is configured to fit inside a test tube and receive whole blood which can be separated by centrifugation into a plasma layer in the proximal end portion, a buffy coat layer in the intermediate portion and a red blood cell portion in the distal portion. The whole blood separator device wherein at least the proximal end portion has an open end. Preferably, the distal end portion also has an open end.

15 Claims, 6 Drawing Sheets

(56) References Cited

U.S. PATENT DOCUMENTS

| | | |
|---|---|---|
| 8,529,957 B2 | 9/2013 | Turzi et al. |
| 9,573,130 B2 | 2/2017 | Hassouneh et al. |
| 9,757,506 B2 | 9/2017 | Jeong et al. |
| 9,833,478 B2 | 12/2017 | Turzi et al. |
| 10,052,349 B2 | 8/2018 | Turzi et al. |
| 10,080,770 B2 | 9/2018 | Turzi et al. |
| 10,092,598 B2 | 10/2018 | Turzi et al. |
| 2013/0045852 A1* | 2/2013 | Chapman ............... B01D 21/26 494/36 |
| 2015/0211966 A1* | 7/2015 | Hsu ........................ A61B 5/154 435/307.1 |
| 2017/0000826 A1* | 1/2017 | Tucker ................... A61K 35/19 |
| 2019/0300848 A1 | 10/2019 | Fagg et al. |

* cited by examiner

WHOLE BLOOD SEPARATOR DEVICE AND METHOD OF USE

FIELD OF THE INVENTION

The present invention relates to a container assembly device for separating components of a fluid by centrifuging, more particularly separating blood components in whole blood.

BACKGROUND OF THE INVENTION

Separating components of a fluid by centrifuging containers is well known. Tubes having a cylindrical shape with an open top and closed hemispherical bottom have been used for such purposes for a long time.

In medical research and medical practice generally the most common fluid to be separated is whole red blood. Whole red blood samples contain heavy weight red blood cells, light weight plasma, and intermediate weight platelets and white blood cells often referred to as the buffy coat. During centrifuging the heaviest component, red blood cells, is spun to the bottom of the container, the buffy coat which appears white is above the red blood cells and the slightly yellow plasma lies at the top.

In many medical applications the goal is to recover the separated plasma or recover the intermediate layer of the platelets and white blood cells or to recover both layers together.

An earlier invention U.S. Pat. No. 3,807,955 entitled, "Serum/Plasma Isolator Cup" was a cup inserted into a tube wherein the serum/plasma was collected from the centrifuged blood and placed in a cup which was snapped into the tube holding the spun red blood cells. The purpose of the invention was to separate the serum/plasma from the red blood cells but still keep the whole sample together to avoid misidentifying or mishandling the sample. The invention did not address the problem of collecting the separated blood components.

Earlier work in U.S. Pat. No. 3,513,976 granted May 26, 1970 entitled, "Leukocyte Flask And Method Of Obtaining White Cells From Whole Blood" showed an hourglass design having two large containers, one being a closed bottom flask portion and one being an open top flask portion separated by a vertical column in the shape of a cylindrical tube. This device allowed the buffy coat to be centrally located in the vertical column below the plasma and above the red blood cells. Many variations of this hourglass design concept have evolved over the years all with the goal of making the collection and separation of the blood components easier.

Some examples are: U.S. Pat. No. 9,757,506 B2 entitled, "Integrated Kit For Separating Blood And Concentrating PRP And Method For Extracting PRP Using The Same" teaches a unique container system having the larger upper and bottom portions with a narrowed intermediate portion. Similarly, U.S. Pat. No. 9,573,130 B2 teaches a similar device in the patent entitled, "Method Of Separating Biological Fluids Into Component Parts Using A Fluids Concentration Cup Assembly With Hourglass Shape".

All these designs have the common desirable hourglass shape in a container of a rather complex and costly design.

The present invention provides a unique and simplified design to achieve the desired blood separation in a more efficient and reliable way as described below.

SUMMARY OF THE INVENTION

A whole blood separator device has a sleeve. The sleeve has a sleeve body. The sleeve body has an enlarged first proximal end portion and an enlarged second distal end portion and an intermediate cylindrical tube portion connecting the first proximal end portion and the second distal end portion. The sleeve body is configured to fit inside a test tube and receive whole blood which can be separated by centrifugation into a plasma layer in the proximal end portion, a buffy coat layer in the intermediate portion and a red blood cell portion in the distal portion. The whole blood separator device wherein at least the proximal end portion has an open end. Preferably, the distal end portion also has an open end.

In one embodiment, the sleeve body is symmetrical, the distal end portion being identical in size and shape relative to the proximal end portion. The intermediate cylindrical tube portion has a diameter smaller than the distal and proximal end portions. The intermediate portion has a length L between the distal or proximal end portions. The sleeve body has a liquid holding volume and the sleeve when fit into the test tube has the red blood cell at or below the intermediate cylindrical tube portion.

The whole blood separator device can include a test tube. The test tube is sized to receive the sleeve body and having an open proximal end and a closed distal end.

In one embodiment, the device includes a pair of elastomeric O-ring seals. One O-ring is configured to fit into a groove on an exterior surface of the proximal end portion and one O-ring is configured to fit into a groove on an exterior surface of the distal end portion. The O-rings, when attached to the grooves on the sleeve body, seal the sleeve body to the test tube at two longitudinally spaced locations when assembled.

The whole blood separator device allows the following method to be practiced. A method of separating whole blood has the steps of: providing a sleeve configured to fit inside a test tube, the sleeve having a proximal end portion, an intermediate portion and a distal end portion; inserting the sleeve inside the test tube to form a whole blood separator device; adding a volume of whole blood to the whole blood separator device; centrifuging the whole blood at 800 to 4000 rpm for 1 to 15 minutes one time to separate the whole blood into a plasma layer, a buffy coat layer and a red blood cell layer; and wherein the plasma layer is in the proximal end portion of the sleeve, the buffy coat layer is in the intermediate portion and the red blood cell layer is in the distal end portion.

The method further has the step of: sealing the sleeve against the inside wall of the test tube by placing O-rings on the sleeve, on O-ring on the proximal end portion and one O-ring on the distal end portion, wherein the O-rings seal against the test tube upon the step of inserting the sleeve into the test tube. The combination of the sleeve and the test tube create a volumetric space for holding the separated blood layers, the proximal end portion in combination with the test tube holding about 50 percent, the intermediate layer holding about 20 percent and the proximal end portion holding the remaining about 30 percent of the separated blood. The buffy coat layer after centrifuging resides in the intermediate layer. The method further has the steps of: recovering the plasma layer by removing from the whole blood separator device or recovering the buffy coat layer by pipetting the buffy coat layer and leaving the plasma layer and the whole blood layer or recovering both the plasma layer and the buffy coat layer together leaving the whole blood layer. The method further has the step of: preparing a PRP preparation by suspending the buffy coat layer in a portion of the plasma layer of about ⅓ to ⅔ mixing and creating a PRP Platelet Rich Plasma preparation and the step of: discarding the ⅓ to ⅔ PPP Plated Poor Plasma and the red blood cells.

BRIEF DESCRIPTION OF THE DRAWINGS

The invention will be described by way of example and with reference to the accompanying drawings in which.

DETAILED DESCRIPTION OF THE INVENTION

Figure 1:
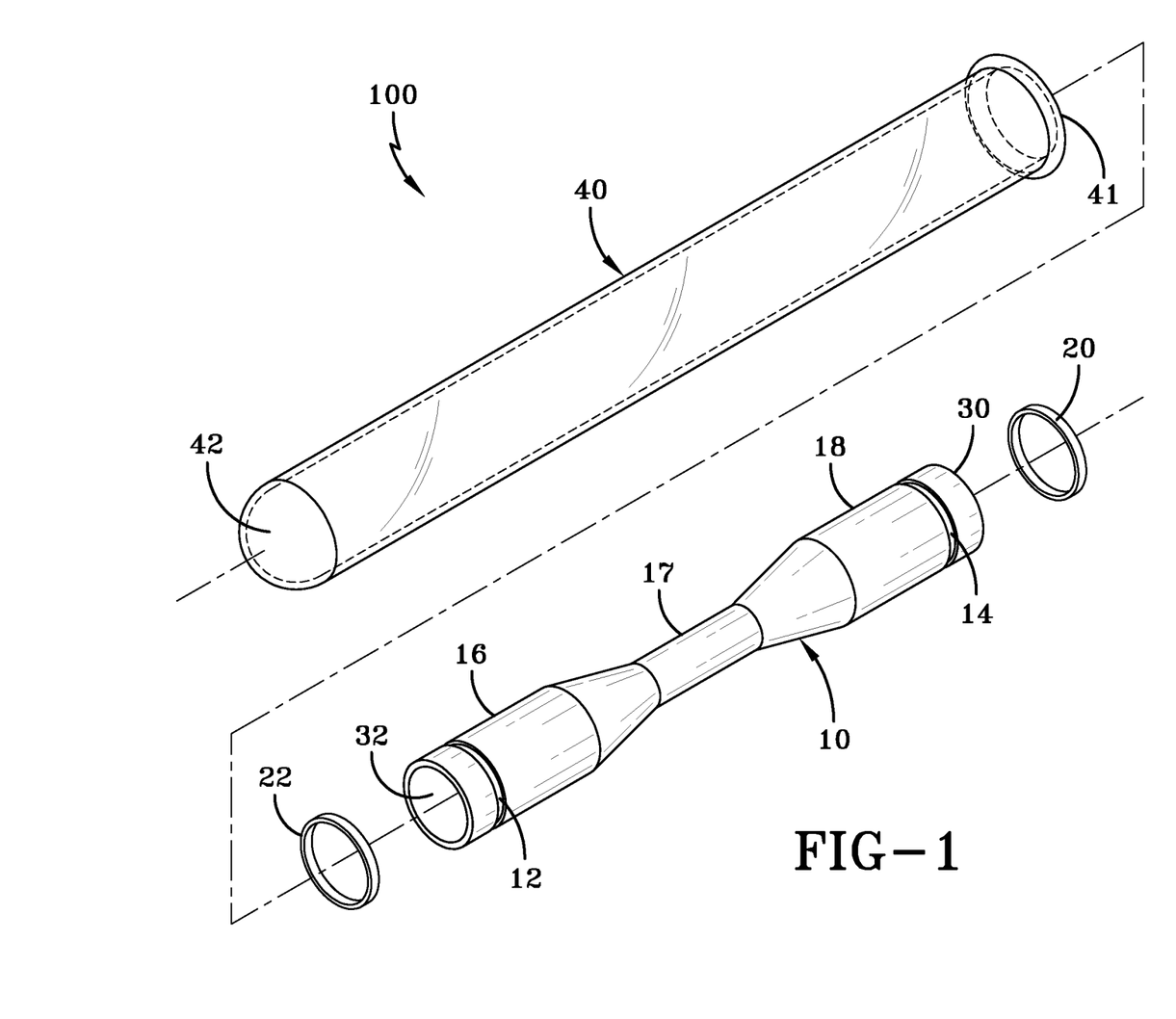
FIG. 1 is an exploded view of the whole blood separator device of the present invention.

With reference to FIGS. 1-4 the whole blood separator device 100 is illustrated. In FIG. 1, an exploded view of the whole blood separator device 100 shows the sleeve body 10, O-rings 20, 22 and test tube 40. The test tube 40 has a closed end 42 and an open end 41. The test tube 40 is sized to allow the sleeve 10 to be inserted inside the test tube 40. As illustrated, the sleeve 10 has a distal end portion 16 with a groove 12 near the end 32 for receiving the O-ring 22. A narrow cylindrical tube shaped intermediate portion 17 connects the distal end portion 16 to a proximal end portion 18. The intermediate portion 17 is a hollow tube elongated longitudinally and provided between the distal end portion 16 and the proximal end portion 18. As shown, the proximal end portion 18 has a groove 14 near the open end 30 to receive the O-ring 20.

The enlarged proximal end portion 18 and the enlarged distal end portion 16 as illustrated are symmetrical and equal in volumetric capacity. This simplifies the molding when manufacturing of the sleeve 10. Alternatively, the end portions 18, 16 may be made asymmetrical with different volumetric capacities. Each has a cylindrical end shape that tapers inwardly in a conical shape to the intermediate section 17. The combination of the sleeve 10 and the tube 40 allows the volume or capacity at the distal end 16 to be defined by the portion 16 and the round bottom base end 42 of the tube 40. At the proximal end 18 of the sleeve 10 the volume is defined by the proximal end portion 18 and the remaining portion of the tube 40 to the end 41 of the tube 40 extending beyond the proximal end 18 of the sleeve 10. This allows the volume of the whole blood sample to be greater than the volume of the sleeve 10 alone. This means the fluid being separated, in this case whole blood, can greatly exceed the sleeve volume while still allowing for a clear demarcation of the buffy coat layer 6 held in the intermediate portion 17.

Figure 2:
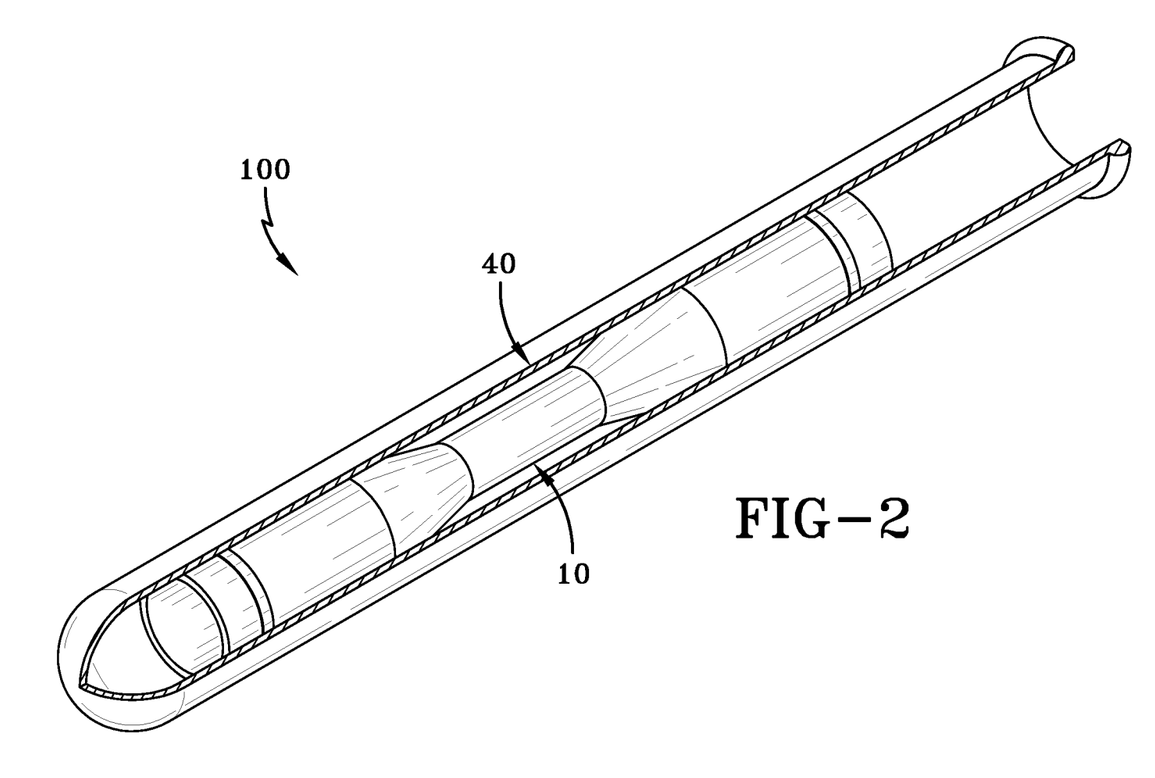
FIG. 2 is a perspective cross-sectional view of the whole blood separator device of the present invention shown assembled.
Figure 3:
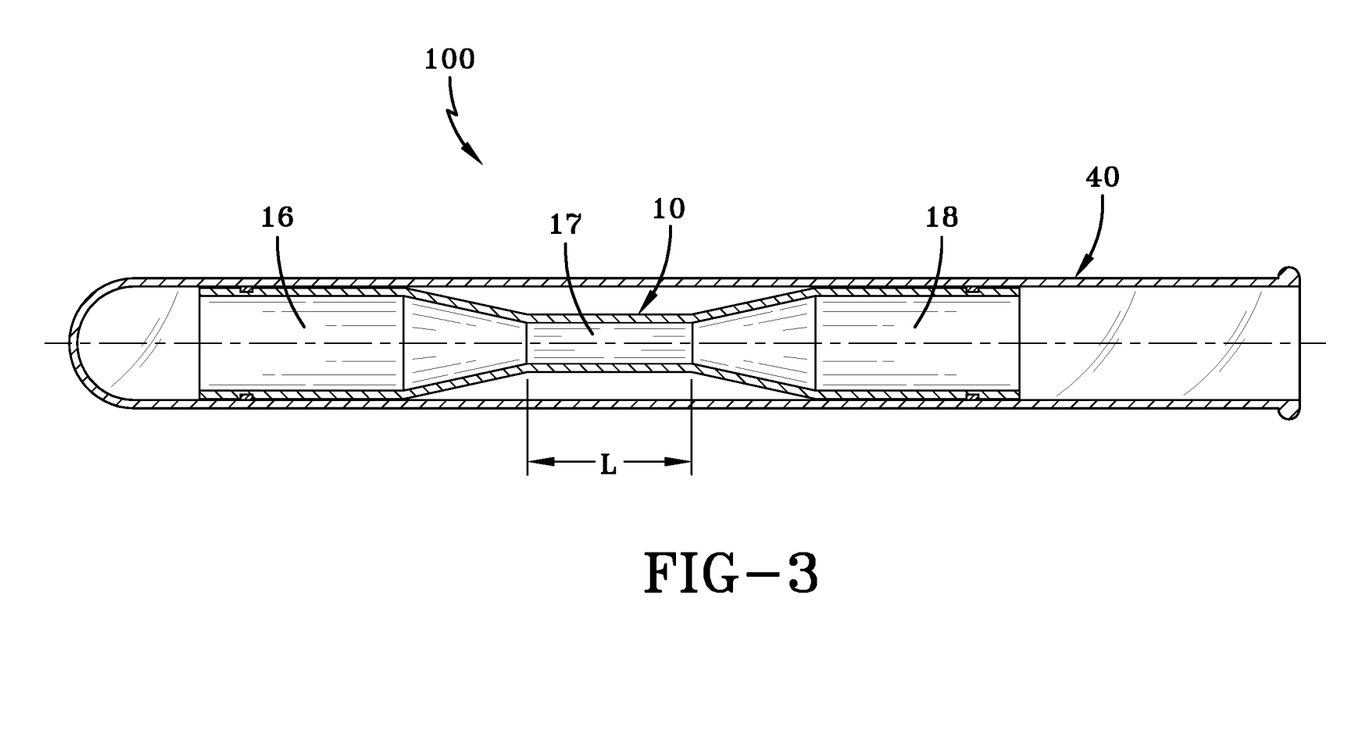
FIG. 3 is a pan cross-sectional view of the whole blood separator device assembled.

With reference to FIG. 2, the sleeve 10 with O-rings 20, 22 is shown inserted into the tube 40. In this position, the sleeve 10 is pushed towards the closed end 42 of the tube 40 and is ready to receive a fluid. This is also shown in plan cross-sectional view FIG. 3.

Figure 4:
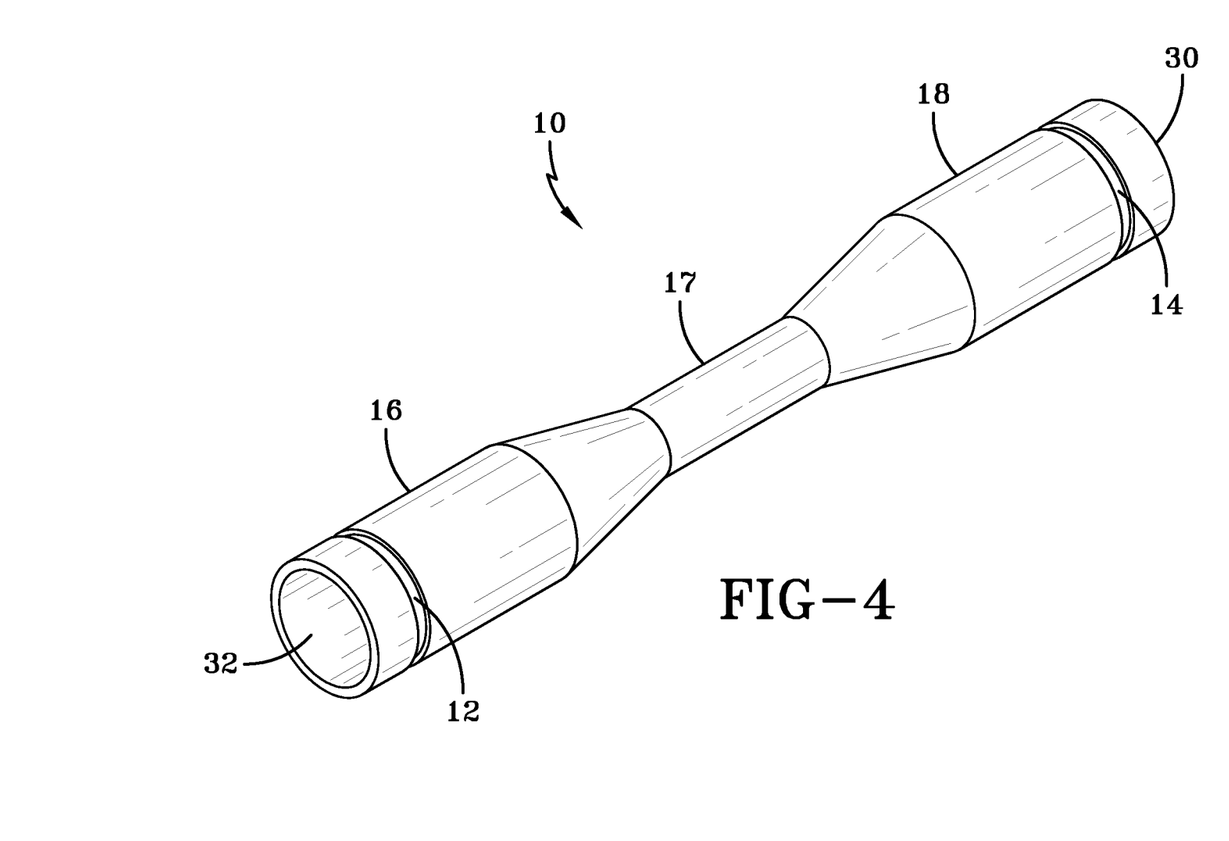
FIG. 4 is a perspective view of the separator sleeve of the whole blood separator device.
Figure 5:
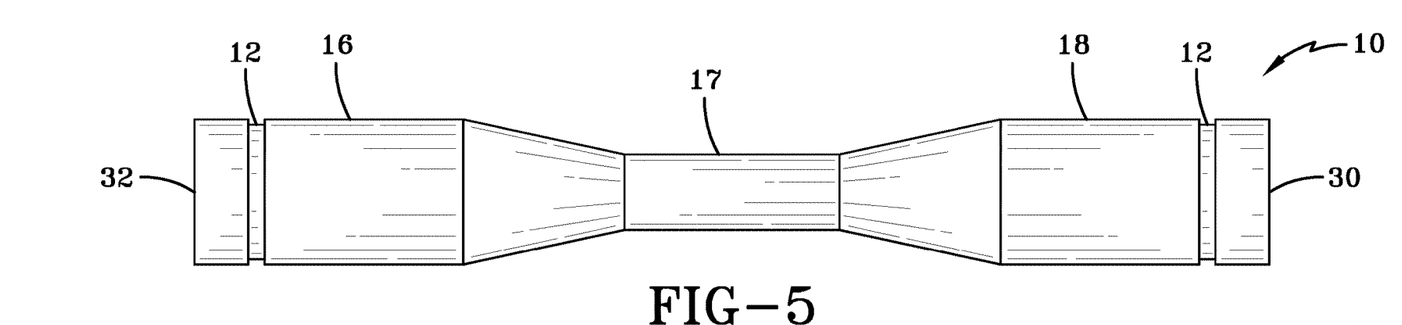
FIG. 5 is a frontal plan view of the separator sleeve of FIG. 4.
Figure 6:
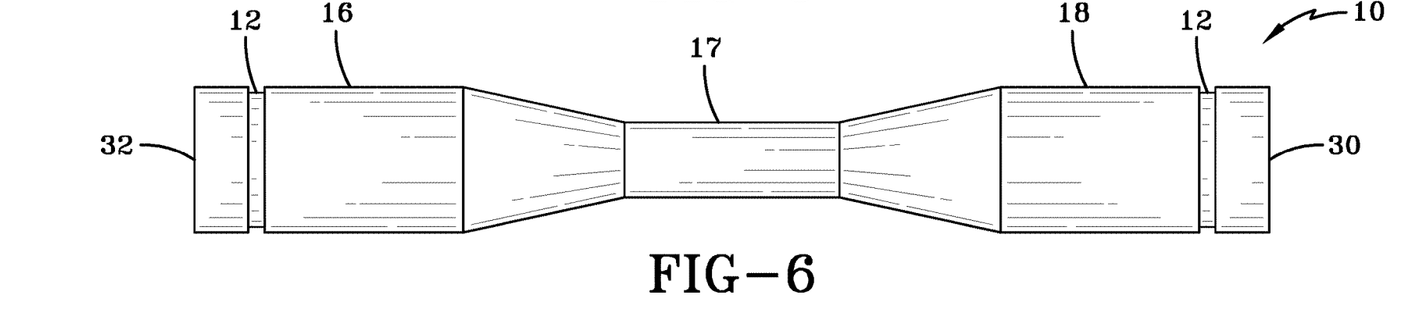
FIG. 6 is a rearward plan view of the separator sleeve.
Figure 7:
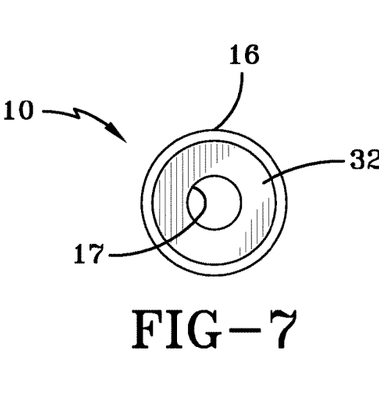
FIG. 7 is a first end view of the separator sleeve.
Figure 8:
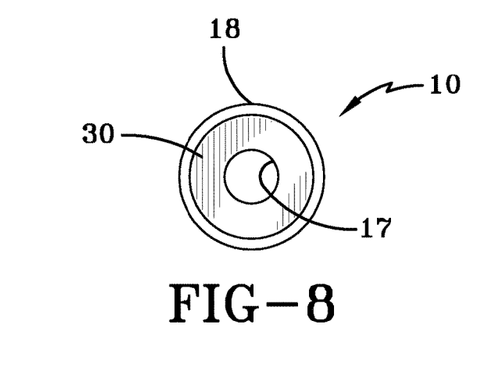
FIG. 8 is a second end view of the separator sleeve.

With reference to FIG. 4, a perspective view of the sleeve 10 is illustrated showing the open ends 30, 32 at the distal end portion 16 and proximal end portion 18 respectively. The sleeve 10 preferably can be made of a clear or translucent material such as plastic, polycarbonate or any clear material, including glass, that will allow the user to be able to see through the test tube 40 and into the sleeve 10 to observe the fluids after separation.

With reference to FIGS. 5-8, the various views of the sleeve 10 are illustrated. As shown, the narrow cylindrical intermediate portion 17 is shown slightly shorter than the distal or proximal end portions 16, 18. The length L of the intermediate portion 17 can be adjusted such that the intermediate portion 17 can insure that the proper fluid layers are positioned relative to the sleeve 10 during whole blood separation.

Figure 9:
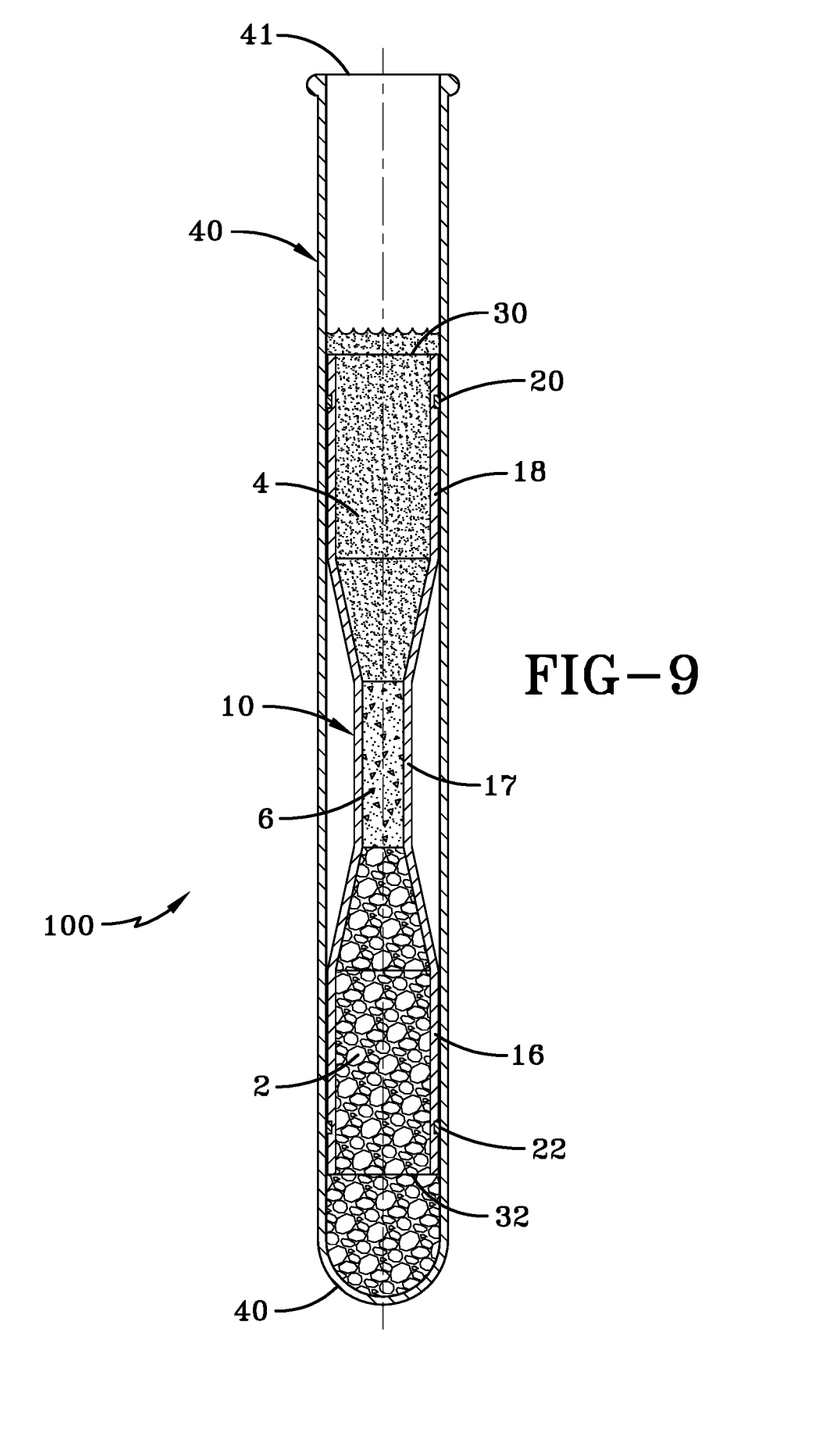
FIG. 9 is a plan view of the whole blood separator device illustrating the blood components after separation.

With reference to FIG. 9, whole blood separator device 100 is shown filled with whole blood that has been centrifuged and separated. In the distal end portion 16 of the device 100, the red blood cell layer 2 is shown. In the intermediate portion 17 the buffy coat layer 6 is shown. At the proximal end portion 18, the plasma layer 4 is shown. These layers are separated by centrifuging the whole blood when the whole blood has been placed into the whole blood separator device 100 and centrifuged at speeds of 800-4000 rpm over a period of time of 1 to 15 minutes.

The present device provides an efficient and relatively inexpensive way to prepare platelet rich plasma PRP from whole blood. The whole blood from the patients will be collected in the tubes 40 with the sleeve 10 inserted with or without anticoagulant. The whole blood separator device 100 may or may not have vacuum like a regular vacutainer. These devices 100 will then be spun in the centrifuge at 800-4000 rpm for 1-15 min. This creates a single spin method which will give 3 layers: a top plasma layer 4, yellow in color; a middle white buffy coat layer 6 containing platelets and white blood cells; and a bottom Red Blood cell layer 2.

The normal hematocrit, proportion of red blood cells, in men is about 38-48% and in women is about 35-45%. The concept is to have the intersection of white buffy coat 6 and red blood cell layer 2 to form after centrifugation in the narrow intermediate portion 17 of the sleeve 10. Dimension wise, the bottom distal portion 16 of the sleeve 10 including the volume to the bottom end 42 of the tube 40 will hold around 30% of the tube 40 volume, the middle intermediate portion of the sleeve 10 will hold around 20% and the proximal portion 18 of the sleeve 10 and the volume of the tube to the upper end 41 of the tube 40 will hold the remaining 50%. This will ensure the intersection will be formed in the narrow intermediate portion 17 of the sleeve 10.

Having the white buffy coat 6 in the middle or intermediate portion 17 of the sleeve 10 will provide more height due to the reduced diameter and thus will allow the physician/surgeon to collect this portion easily. Normally for PRP, platelet rich plasma preparation, the bottom layer, which is the RBC, red blood cell, layer 2 is not collected. Some physicians will just suspend the buffy coat 6 in the entire top plasma layer 4 and use it for injection. In some cases, they will discard ⅓-⅔ of the top plasma 4 called platelet poor plasma (PPP). They will then suspend the white buffy coat 6 in the remaining plasma 4 and that mixture is then called Platelet Rich Plasma (PRP). The whole blood separator device 100 allows the physician to use either method. In addition, due to the increased height in the intermediate portion 17, the physician will have ease of collection of whole or part of the white buffy coat layer 6, allowing the physician to control the amount of platelets and white blood cells the physician intended to have in the final PRP dose.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A whole blood separator device comprises:
   a sleeve, the sleeve having a sleeve body and having an enlarged first proximal end portion and an enlarged second distal end portion, the proximal end portion has an open end and the distal end portion has an open end each end portion tapers inwardly in a conical shape to an intermediate cylindrical tube portion connecting the first proximal end portion and the second distal end portion, the intermediate cylindrical tube portion has a diameter smaller than the distal and proximal end portions, the sleeve body has a liquid holding volume;
   a test tube configured to receive the sleeve, wherein the combination of the test tube and the sleeve are configured hold a volume of whole blood and wherein the intermediate cylindrical tube portion holds around 20 percent of the whole blood volume and the distal and proximal end portions in combination with the test tube hold the remaining around 80 percent of the whole blood volume, wherein the whole blood volume is equal to or greater than the liquid holding volume of the sleeve; and
   wherein the sleeve body is configured to fit inside the test tube and receive whole blood which can be separated by centrifugation into a plasma layer in the proximal end portion, a buffy coat layer in the intermediate cylindrical tube portion and a red blood cell portion in the distal portion.

2. The whole blood separator device of claim 1 wherein the sleeve body is symmetrical, the distal end portion being identical in size and shape relative to the proximal end portion.

3. The whole blood separator device of claim 1 wherein the intermediate portion has a length L between the distal and proximal end portions.

4. The whole blood separator device of claim 3 wherein the sleeve body has a liquid holding volume and the sleeve when fit into the test tube has the red blood cell at or below the intermediate cylindrical tube portion.

5. The whole blood separator device of claim 1 further comprises:
   a pair of elastomeric O-ring seals, one O-ring configured to fit into a groove on an exterior surface of the proximal end portion and one O-ring configured to fit into a groove on an exterior surface of the distal end portion.

6. The whole blood separator device of claim 5 wherein the O-rings when attached to the grooves on the sleeve body seal the sleeve body to an inner surface of the test tube at two longitudinally spaced locations.

7. A method of separating whole blood comprises the steps of:
   providing a sleeve configured to fit inside a test tube, the sleeve having a proximal end portion with an open end, an intermediate cylindrical tube portion and a distal end portion with an open end;
   inserting the sleeve inside the test tube to form a whole blood separator device, wherein the combination of the test tube and the sleeve is configured to hold a volume of whole blood and wherein the intermediate cylindrical tube portion holds around 20 percent of the whole blood volume and the distal and proximal end portions in combination with the test tube hold the remaining around 80 percent of the whole blood volume, wherein the whole blood volume is equal to or greater than the liquid holding volume of the sleeve;
   adding a volume of whole blood to the whole blood separator device;
   centrifuging the whole blood at 800 to 4000 rpm for 1 to 15 minutes one time to separate the whole blood into a plasma layer, a buffy coat layer and a red blood cell layer; and
   wherein the plasma layer is in the proximal end portion of the sleeve, the buffy coat layer is in the intermediate portion and the red blood cell layer is in the distal end portion.

8. The method of claim 7 further comprises the step of: sealing the sleeve against the inside wall of the test tube by placing O-rings on the sleeve, one O-ring on the proximal end portion and one O-ring on the distal end portion, wherein the O-rings seal against the test tube upon the step of inserting the sleeve into the test tube.

9. The method of claim 7 wherein the combination of the sleeve and the test tube create a volumetric space for holding the separated blood layers, the proximal end portion in combination with the test tube holding about 50 percent, the intermediate layer holding about 20 percent and the distal end portion in combination with the test tube holding the remaining about 30 percent of the separated blood.

10. The method of claim 9 wherein the buffy coat layer after centrifuging resides in the intermediate layer.

11. The method of claim 7 further comprises the step of: recovering the plasma layer by removing from the whole blood separator device.

12. The method of claim 7 further comprises the step of: recovering the buffy coat layer by pipetting the buffy coat layer and leaving the plasma layer and the whole blood layer.

13. The method of claim 7 further comprises the step of: recovering both the plasma layer and the buffy coat layer together leaving the whole blood layer.

14. The method of claim 7 further comprises the step of: preparing a PRP preparation by suspending the buffy coat layer in the plasma layer creating the PRP Platelet Rich Plasma preparation.

15. The method of claim 14 further comprises the step of: discarding a top ⅓ to ⅔ of the plasma layer containing PPP Plated Platelet Poor Plasma prior to suspending the buffy coat layer in the plasma layer to create the PRP Platelet Rich Plasma discarding the red blood cells in the bottom layer.

* * * * *